(12) United States Patent
Morsi

(10) Patent No.: US 7,468,072 B2
(45) Date of Patent: Dec. 23, 2008

(54) ENDOVASCULAR BALLOON GRAFT

(76) Inventor: Hesham Morsi, 2058 Southgate Blvd., Houston, TX (US) 77030

( * ) Notice: Subject to any disclaimer, the term of this patent is extended or adjusted under 35 U.S.C. 154(b) by 395 days.

(21) Appl. No.: 10/540,999

(22) PCT Filed: Dec. 27, 2003

(86) PCT No.: PCT/US03/41317
§ 371 (c)(1),
(2), (4) Date: Jun. 28, 2005

(87) PCT Pub. No.: WO2004/060214
PCT Pub. Date: Jul. 22, 2004

(65) Prior Publication Data
US 2006/0206197 A1    Sep. 14, 2006

Related U.S. Application Data

(60) Provisional application No. 60/437,092, filed on Dec. 30, 2002.

(51) Int. Cl.
*A61F 2/06* (2006.01)
(52) U.S. Cl. ............... 623/1.25; 623/1.32; 623/1.24; 623/903
(58) Field of Classification Search ....... 623/1.23–1.25, 623/1.28, 1.32, 1.44
See application file for complete search history.

(56) References Cited

U.S. PATENT DOCUMENTS

| | | | | |
|---|---|---|---|---|
| 4,183,102 A | * | 1/1980 | Guiset | 623/1.25 |
| 5,330,528 A | * | 7/1994 | Lazim | 623/1.25 |
| 5,370,691 A | * | 12/1994 | Samson | 623/1.22 |
| 5,607,468 A | | 3/1997 | Rogers et al. | |
| 5,871,537 A | | 2/1999 | Holman et al. | |
| 6,312,462 B1 | | 11/2001 | McDermott et al. | |
| 6,319,276 B1 | * | 11/2001 | Holman et al. | 623/1.11 |
| 6,706,064 B1 | | 3/2004 | Anson | |
| 2003/0093145 A1 | | 5/2003 | Lawrence-Brown | |
| 2003/0116260 A1 | | 6/2003 | Chobotov et al. | |
| 2003/0120338 A1 | | 6/2003 | Chobotov et al. | |
| 2003/0212384 A1 | | 11/2003 | Hayden | |
| 2004/0019322 A1 | | 1/2004 | Hoffmann | |

* cited by examiner

*Primary Examiner*—William H. Matthews
*Assistant Examiner*—Suba Ganesan
(74) *Attorney, Agent, or Firm*—Law Office of David McEwing PC

(57) ABSTRACT

A method and apparatus for repair of stenotic and aneurysmic vessels utilizing in situ deployment of an inflatable tubular shaped device (1) having a longitudinally oriented annulus (17). When inflated, the size and rigidity of the device (1) is increased, thereby providing supplemental strength to the vessel wall and a lumen (8) for the passage of fluid.

16 Claims, 6 Drawing Sheets

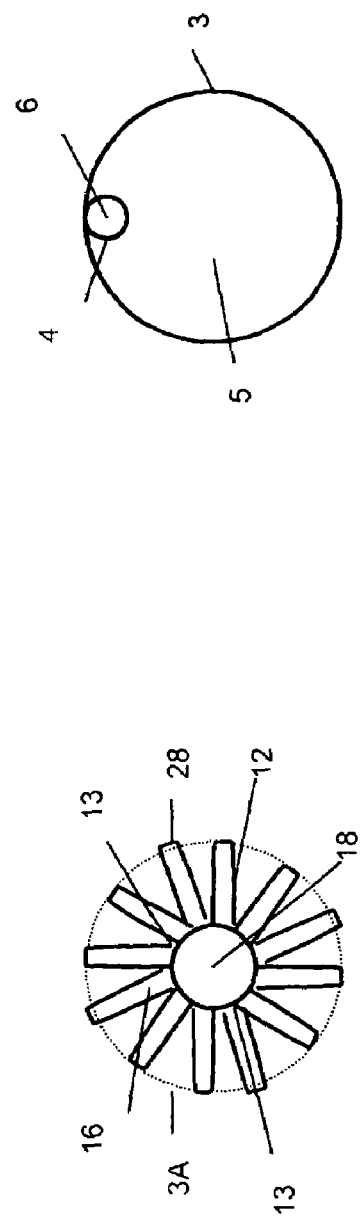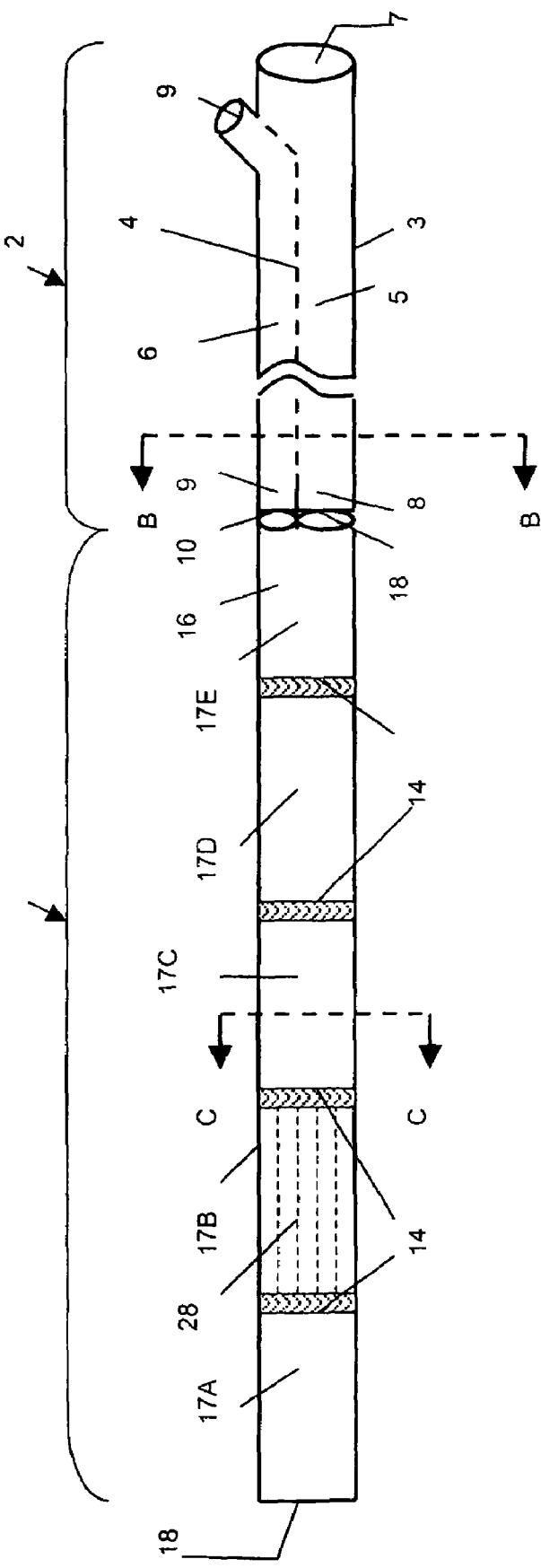

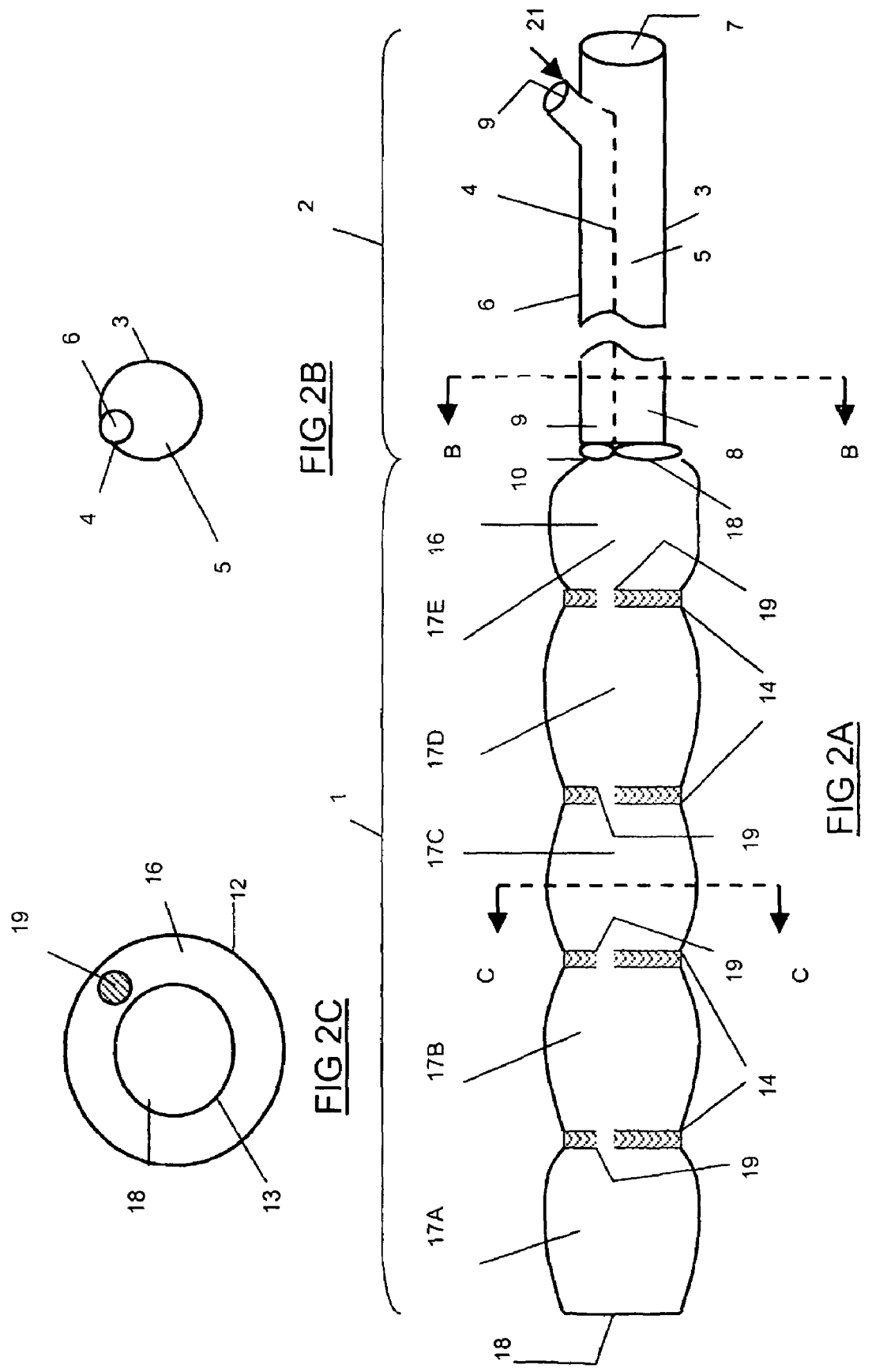

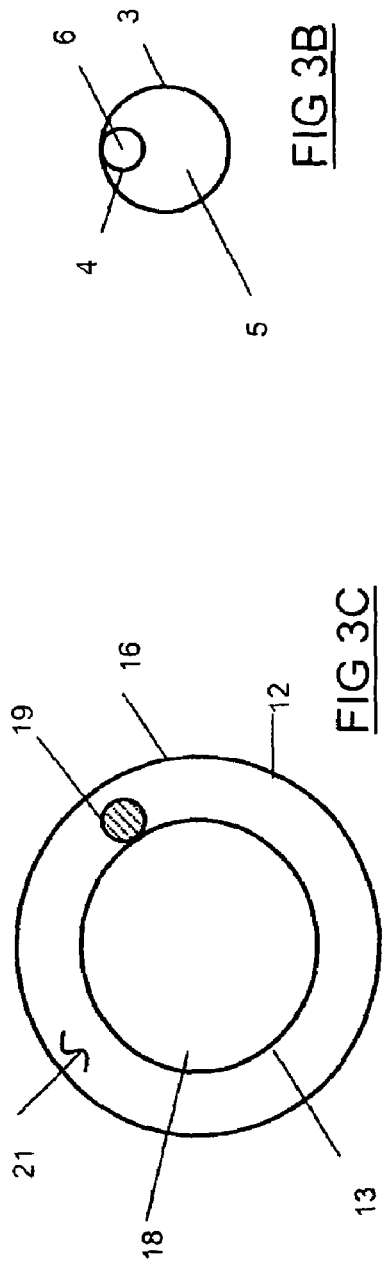
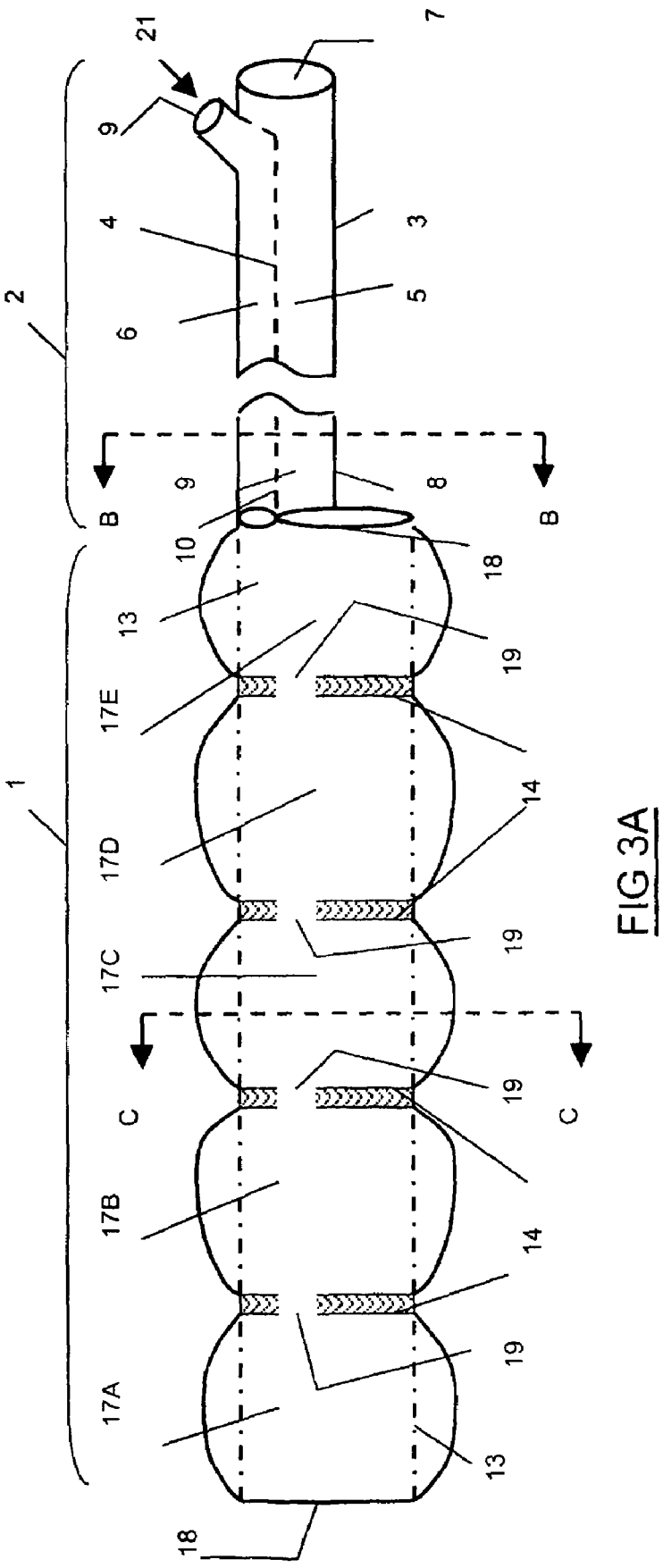
FIG 3B
FIG 3C
FIG 3A

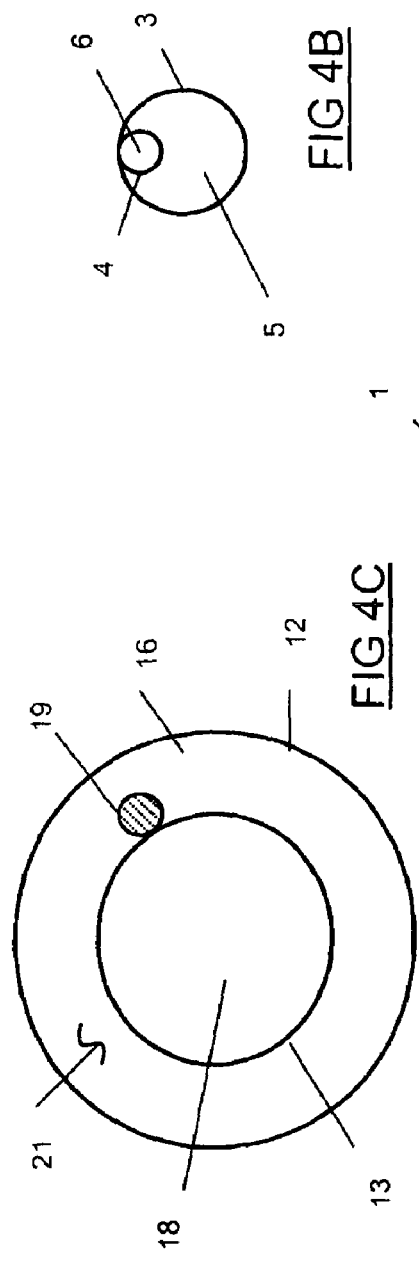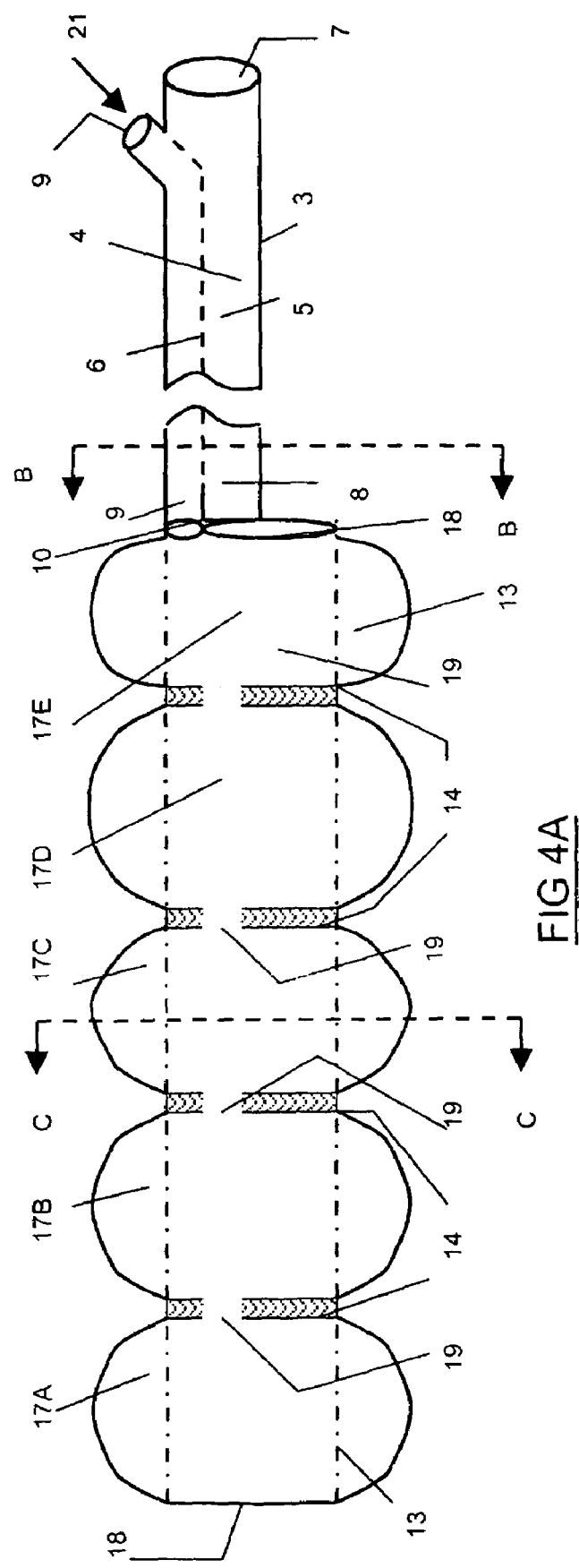

ENDOVASCULAR BALLOON GRAFT

CROSS REFERENCE TO RELATED APPLICATION

This application claims the benefit of and priority to U.S. Provisional Application No. 60/437,092 entitled "Morsi Balloon Graft" and filed Dec. 30, 2002

BACKGROUND OF INVENTION

1. Field of Use

The invention pertains to a graft design that combines the minimal size and increased flexibility in its deliverable form which allows for successful navigation of torturous, stenotic blood vessels, aneurysms and other body passages with an in situ increase in size and rigidity, thus improving upon the current covered stent in treatment of various diseases such as atherosclerosis and aneurysms. The invention can be utilized in both the cerebral or peripheral circulatory system.

2. Prior Art

Inflatable devices for opening stenotic blood vessels are known. Devices such as angioplasty balloons, however, are unsuitable for permanent placement since the balloon component is fused to the catheter. Removal of the catheter will cause the collapse of the balloon. Further, the balloon itself may obstruct the lumen of the artery. Further, the procedure usually requires two separate steps; the first clearing of the occlusion and, second, the placement of a reinforcing stent with increased risk of embolization and the risk of restenosis. Currently metallic stents covered with a membrane are often installed as the second step.

Devices for treatment of aneurysms may not provide sufficient wall support or, alternatively, have material properties hindering their deployment within the affected portion of a vessel. Other devices may be subject to dislocation by the mechanics of fluid flow and pressure. Further, other devices of treating aneurysms, such as coils, are not suitable for certain types of aneurysms, e.g., wide neck or fusiform aneurysms. They may also be subject to incomplete olbiteration of the aneurysm or coil compaction which may result in re-growth of the aneurysm and future rupture. Devices that are of a braid type construction are subject to variations of the longitudinal length in relation to radial expansion.

SUMMARY OF INVENTION

The invention pertains to a method and apparatus for the repair of stenotic vessels utilizing an inflatable device that can open the occlusion with minimized occurrence of residue breaking free within the blood flow, thereby risking injury to another part of the body, while simultaneously creating a smooth interior walled lumen but with an undulating or corrugated outer wall surface to facilitate secure placement within the intended portion of the vessel. The device also can be moved into position while in a collapsed state, thereby minimizing disruption or irritation of the lumen, and subsequently inflated to create a substantially flexible but stiff walled shent capable of contouring to the shape of the lumen without collapse or buckling.

The device subject of the invention decreases the risk of distal embolization by providing a single system that performs both balloon angioplasty and delivery of the graft in a relatively easy fashion. The flexible nature of the device during deployment allows precise positioning and with no risk of shortening as the length of the graft remains fixed during expansion and deployment. In addition, the device subject of the invention can be retrievable and is compatible with MRI diagnostic testing.

The invention also pertains to a method and apparatus for repairing aneurysm vessels by providing a graft design that, when deployed across the aneurysm, will effectively exclude the aneurysm from circulation and reinforce the weak blood vessel wall. This minimizes possible re-growth or recanalization. It will be appreciated that the operation of the invention reinforces the blood vessel wall both at the location of the aneurysm and in the proximate surrounding area.

The method taught be the invention further decreases the time and cost of the procedure. The method further permits good visualization of the graft during and after deployment through the use of radio-opaque inflating materials. The device and method of the invention also decreases the risk of intimal hyperplasia and resenosis.

Other benefits of the invention will also become apparent to those skilled in the art and such advantages and benefits are included within the scope of this invention.

SUMMARY OF DRAWINGS

The accompanying drawings, which are incorporated in and constitute a part of the specification, illustrate preferred embodiments of the invention. These drawings, together with the general description of the invention given above and the detailed description of the preferred embodiments given below, serve to explain the principles of the invention.

FIG. 1A illustrates the duel lumen catheter utilized to install the device.

FIG. 1B illustrates a cross sectional view of the catheter.

FIG. 1C illustrates a cross sectional view of the invention.

FIG. 2A illustrations the use of the catheter for inflating the invention.

FIG. 2B illustrates a cross sectional view of the catheter.

FIG. 2C illustrates a cross sectional view of the device during deployment.

FIGS. 3A, 3B & 3C illustrate the catheter and the invention in the process of inflation.

FIGS. 4A, 4B & 4C illustrate the catheter and invention after completion of the inflation step.

DETAILED DESCRIPTION OF INVENTION

Figure 1D:
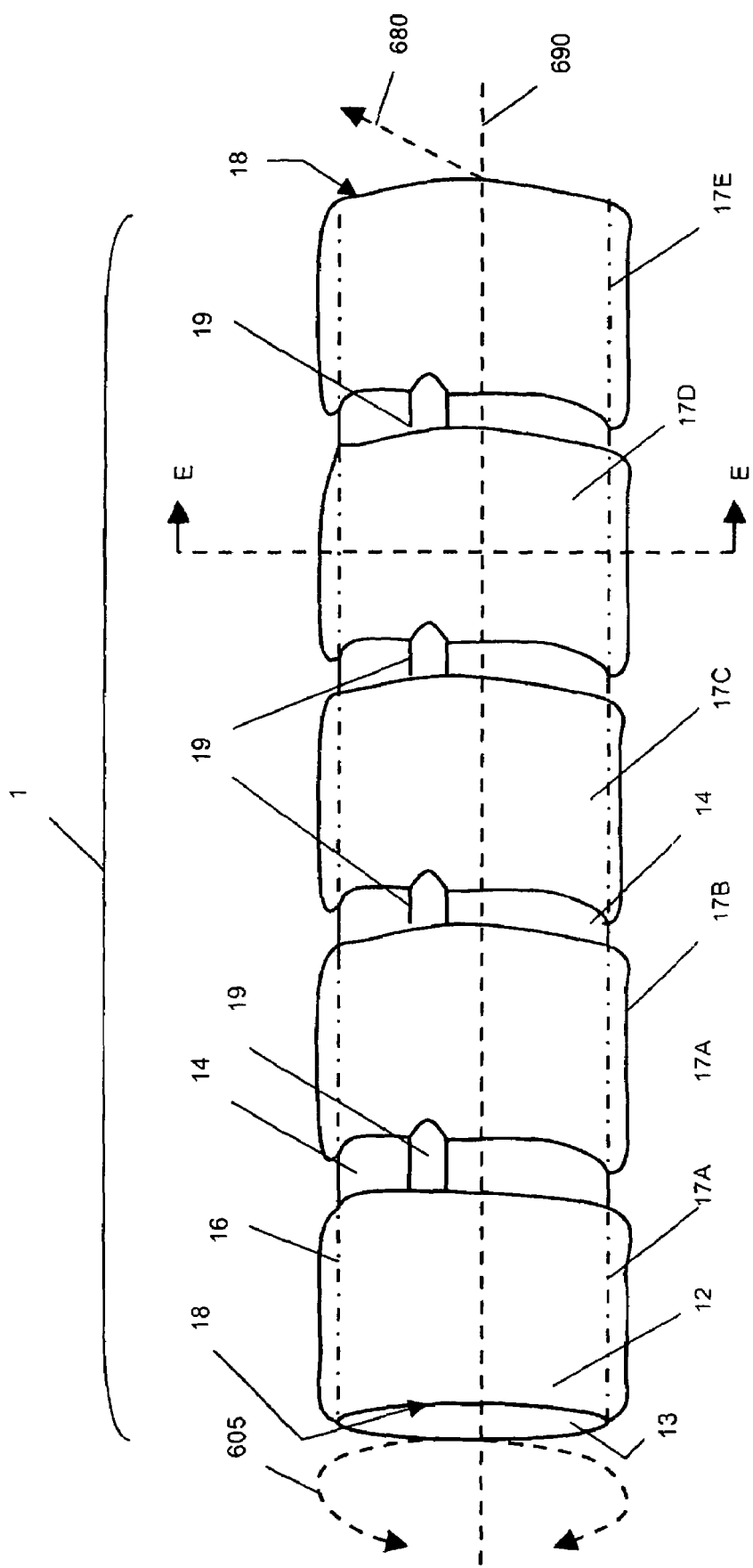
FIG. 1D is a perspective view of the invention.

The above general description and the following detailed description are merely illustrative of the subject invention and additional modes, advantages and particulars of this invention will be readily suggested to those skilled in the art without departing from the spirit and scope of the invention.

FIG. 1A illustrates the system of the invention, being composed of a distal segment 1, which represents the expandable graft and a proximal segment 2, which represents the delivery catheter. The catheter 2 has a double lumen shaft 3. FIG. 1B illustrates a cross sectional schematic of the catheter at a vector arrow BB in FIG. 1A. As shown in FIGS. 1A and 1B, the larger lumen 5 has an aperture proximally 7, and opens distally 8 into the lumen 18 of the distal segment that provides an artificial flow path for the body lumen. Through this lumen, a guiding wire (not shown) can be inserted to facilitate proper positioning of the graft at the desired location in the cerebral or peripheral circulatory system and also to maintain the elongated shape of the graft during insertion.

The smaller catheter lumen 6 has an aperture proximal 9 that can be attached to an inflating device. Distally it is attached to, and in fluid communication with, the fluid tight chambers 16 within segments 17A, 17B, 17C, 17D 17E inside the graft 1 through a detachable check valve 10.

FIG. 1C is a cross sectional schematic view of the collapsed graft at vector arrow CC in FIG. 1A. The graft is completely deflated and folded to a circumference 3A equal to the diameter 3 of the catherter in FIG. 1B. FIG. 1C also illustrates the inner wall 13 of the graft, the outer wall surface 12, folds 28 of the outer graft wall, the collapsed chambers 16 and the lumen 18 of the graft. The longitudinal orientation of the folds 28 of the graft is shown in one segment 17B of FIG. 1A.

The graft 1, in its preferred embodiment is a double walled graft made of a bio-compatible, non-compliant non-porous material from a variety of suitable polymers, such as polyethylene, polyurethane, TFE, PTFE and ePTFE. In the preferred embodiment of the invention, the device, when inflated, forms a predetermined shape and size without becoming distorted. However, it will be appreciated that in other applications, a controlled elasticity of the device in one or more directions with inflation may be desirable. The double wall construction of the device is illustrated in FIGS. 1D, 1E and 1F discussed below.

Figure 1E:
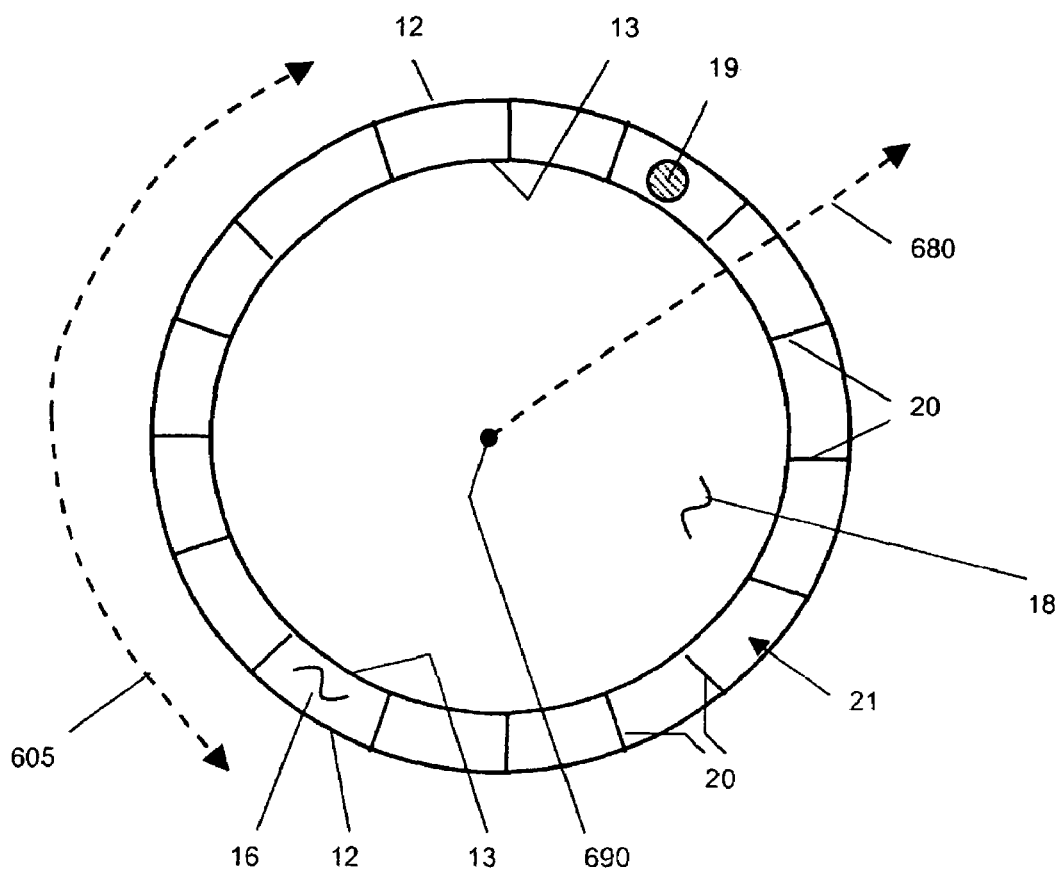
FIG. 1E is an axial cross sectional view of the inflated device showing internal webbing.
Figure 1F:
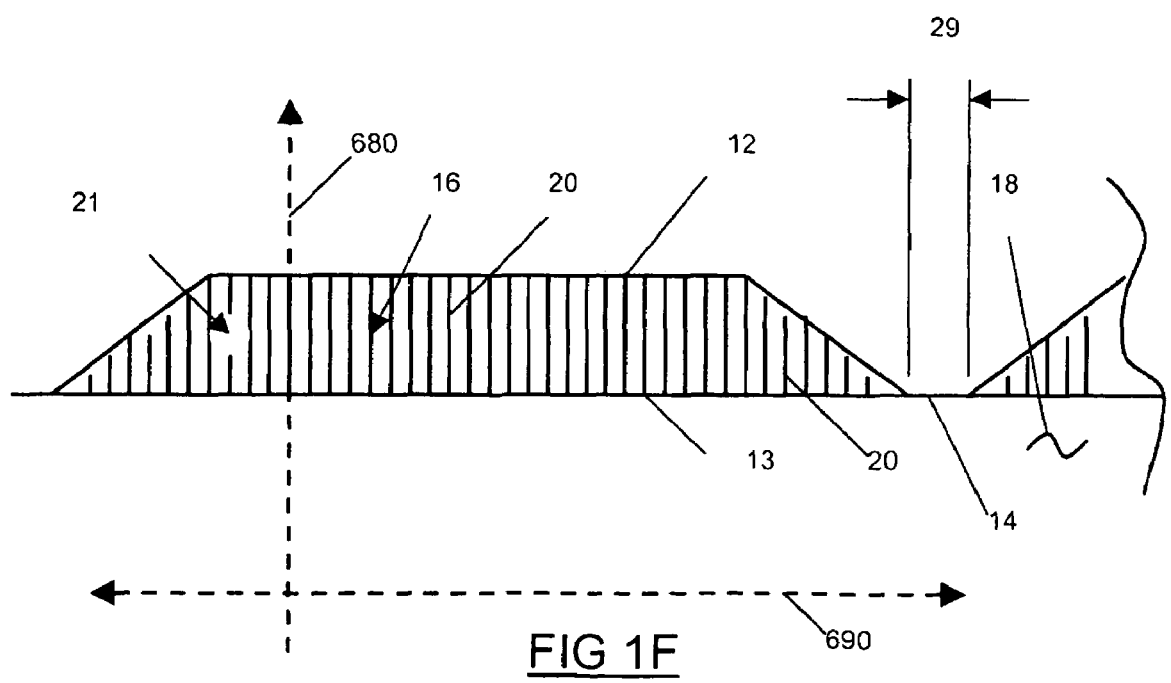
FIG. 1F is a circumferential cross sectional view of the inflated device.

In the preferred embodiment of the invention as illustrated in FIGS. 1D, 1E and 1F, the outer wall 12 is circumferentially 605 and longitudinally 690 larger than the inner wall 13. This is particularly illustrated in FIG. 1F, which also illustrates the internal support struts or webs 20 within the chamber 16. Again, it is within these chambers that that the inflating fluid 21 is deployed. The construction of the inner and outer wall described above allows the inner wall 13 to retain a relatively smooth surface facilitating unimpeded blood flow and the outer wall surface 13 to form a corrugated surface facilitating the shent device to adhere to the vessel wall. These contrasting surfaces 12 13 are illustrated in FIG. 1D.

The two walls 12 13 are completely sealed together both distally and proximally to form the fluid tight chambers 16 that is only attached to, and in fluid communication with, the smaller lumen of the delivery catheter through a detachable check valve 10. Each graft segment 17 comprising the invention contains a fluid tight chamber 16 interconnected by pathways 19 and through which the inflating fluid 21 is conveyed.

The walls are also interconnected by network of integral radially oriented support or retention webs. The radial 680 orientation of the web structure 20 is illustrated in FIGS. 1E and 1F. The radial oriented web network is preferably of equal length through out the whole length of the individual chamber 16 except at the periphery of the chamber where the web structure tapers in length toward the non-expansive junction. The graft design allows a significant portion of the graft wall to be stiffened with the fluid, thereby providing desired strength from collapse of the body lumen.

FIGS. 1D and 1F further illustrate the inner and outer walls to be circumferentially joined together at multiple restricted or non-expandable junctures 14. These fused juncture may be spaced equally throughout the length of the graft 1, thus dividing the inner chamber of the graft into the multiple smaller fluid tight chambers 16 which may of equal linked segments 17A, 1B, 17C, 17D 17E. Each chamber is connected with, and in fluid communication with, the adjacent chamber through one of more valves or holes 19 located in the fused junctures. These fluid communication channels may, or may not, have a common longitudinal orientation. (FIG. 1D illustrates an embodiment having common longitudinal orientation.)

FIG. 1D illustrates the fully deployed graft. The outward radial expansion of the individual segments 17A, 1B, 17C, 17D 17E has been exaggerated for clarity of illustration. Also illustrated are vector arrows or lines showing the longitudinal 690 orientation, radial 680 orientation, and circumferential 605 orientation of the invention as described in this specification.

FIG. 1E illustrates an axial cross section of a chamber of the invention, illustrating the multiple webs 20 that may be used to join the two walls together throughout the circumference of the chamber. This configuration ensures that the graft thoroughly inflates to a pre-selected shape without distortion; with a smooth inner surface, a thin film-like lumen, and a corrugated outer surface, which will anchor the graft to the inside of the blood vessel and prevents the drag force of the flowing blood through the graft form displacing the graft.

FIG. 1F illustrates a longitudinally oriented cross section of a chamber showing the tapered length of the web structure 20, the fused juncture 14 of the inner 13 and outer 12 wall. It will be appreciated that the inflation/stiffing fluid 21 fills the interstitial space FIG. 1F also illustrates the junctures 14 to be very small in width (about one millimeter 29. The juncture is formed by the outer wall 12 fused to the inner wall 13. The outer wall 12 forms an acute angle with the inner wall 13 at the fused juncture 14 as shown if FIG. 1F. They serve both as conduit that connects the adjacent chambers 16 through multiple holes 19 within, and as bending areas (as they do not expand or pressurized when the graft is fully inflated) thus giving the graft some flexibility between the fully inflated segments 17A 17B 17C, 17D, 17E; allowing it to conform to the shape of the blood vessel without the risk of kinking or distortion. They also provide a space on its outer surface for neointimal growth that will further help anchoring and stabilizing the graft. It will be appreciated that the design selection of the segments and junctures may facilitate deployment of the device within varying vessel diameters, tissue structure or architecture. In other embodiments, side fenestrations may be created at selected locations of the invention to allow deployment of across bifurcating blood vessels without compromising blood flow.

It will be further appreciated that the material may selectively include fiber reinforcement, particularly in applications where the device may be subjected to repetitively varying pressures. Such fiber may be presumably installed in a circumferential orientation, but other designs may be found advantageous.

FIGS. 1A and 1C illustrate the graft at the start of deployment and during that portion of the procedure for placing the graft in the selected location within the body lumen. The graft is completely deflated and evacuated from any air and folded throughout its length in longitudinal folds 28 around the lumen 18 in a radial fashion to a circumference 3A approximating the circumference 3 of the delivery catheter 2, illustrated in FIG. 1B. A very thin sheath (not shown) can cover the outer surface of the graft; alternatively, the edges 28 of the longitudinal folds can be loosely adherent together to help maintain the longitudinal shape and smooth outer surface of the graft during insertion.

The proximal end of the graft is tightly packed into a groove (not shown) on the opposing end of the delivery catheter wall.

FIGS. 2A, 2C, 3A, 3C 4A and 4C sequentially illustrated the deployment of the graft in a selected location by the addition of a specified fluid 21 through the catheter 2. The graft has an elongated cylindrical shape when fully inflated and pressurized and has a lumen 18 therein, which provides an artificial flow path for the body lumen (not shown). It is composed of an outer wall 12, and an inner wall 13, wherein the filler material 21 is provided between the two walls to inflate the graft into its predetermined inflated size and shape. Also illustrated is the fluid communication pathway 19 existing between segments 17A, 1B, 17C, 17D 17E. The fluid can be a curable resin system, thereby providing additional stiffening reinforcement to the vessel walls. In addition, the fluid system may also adhere to the inner walls of each segment comprising the invention.

FIGS. 2, 3, & 4 explain the method of the invention. Using fixed radio-opaque markers at both ends of the graft 24, the graft can be perfectly positioned at the desired location within the human lumen (not shown). The graft is deployed by injecting a fluid or gel material of contrast media, monomer, or uncrossed polymer through a pressure monitoring inflation device attached to the proximal end of the small lumen of the delivery catheter, which gradually fills the small catheter lumen 21, and flows across the detachable valve into the chambers of the graft in a successive fashion 22. The fluid may be a curable polymer resin system.

As the chambers of the graft fill gradually, the graft starts to unfold 23 and expand 25 in a radial fashion outward. After the graft expands to its predetermined shape and size 26, a slight increase in the amount of the injected material will lead to increased pressure inside the graft, and exert a sufficient radial force outward, thus becoming axially and sealingly fixed to the inside of the blood vessel.

The graft can then be detached from the delivery catheter 27 through the detachable valve leaving the graft fully expanded and pressurized. This graft design functions as a covert stent graft for treating diseases such as atherosclerosis and aneurysms.

This specification is to be construed as illustrative only and is for the purpose of teaching those skilled in the art the manner of carrying out the invention. It is to be understood that the forms of the invention herein shown and describe are to be taken as the presently preferred embodiments. As already stated, various changes may be made in the shape, size and arrangement of components or adjustments made in the steps of the method without departing from the scope of this invention. For example, equivalent elements may be substituted for those illustrated and described herein and certain features of the invention may be utilized independently of the use of other features, all as would be apparent to one skilled in the art after having the benefit of this description of the invention.

Further modifications and alternative embodiments of this invention will be apparent to those skilled in the art in view of this specification.

I claim:

1. An inflatable graft for placement through tortuous, narrow or stenotic cerebral blood vessels comprising:
   a. a first outer wall of non-compliant material having a proximal end and a distal end;
   b. a second inner wall of non-compliant material having a smaller diameter than the first outer wall and having a proximal end and a distal end;
   c. a fluid tight seal of the first outer wall and the second inner wall at the distal and proximal ends;
   d. at least one or more fused junctures of the first and second wall, each non-inflatable fused juncture forming a circumference with a fixed diameter around the graft and not subject to inflation pressure wherein the graft can bend without kinking or distortion and that create fluid tight seals and fluid communicating passages to each resulting multiple fluid chambers between the said first and said second wall and the said multiple fused junctures;
   e. a valve to convey fluid into the interstitial space to inflate the graft to a pre-selected shape without distortion and create a smooth inner wall lumen;
   f. a plurality of radially oriented separate and narrow non-distorting web support attached to the second inner wall and first outer wall within one or more non-compliant fluid chambers and further comprising tapered web support proximate to the fused junctures and causing the outer wall to taper to the fused juncture and form an acute angle to the cerebral blood vessel wall to dissipate dragging forces of flowing blood through the graft displacing the graft and to provide sites for neointimal growth; and
   g. the inflated first outer wall dimensioned to conform to the shape of the said cerebral blood vessel.

2. The graft of claim 1 further comprising a design selection of the segments and junctures to facilitate deployment of the device within varying vessel diameters, tissue structure or architecture.

3. The graft of claim 1 wherein the outer wall has a greater longitudinal length between each fused joint than the longitudinal length of the inner wall.

4. The graft of claim 1 wherein at least one wall is comprised of a material selected from a group consisting of polyethylene, polyurethane, tetrafluoroethylene, polytetrafluoroethylene and expanded polytetrafluoroethylene.

5. The graft of claim 1 further comprising a fluid that can be communicated through the valve to fill the fluid chambers.

6. The graft of claim 5 wherein after the fluid chamber is filled with fluid, the outer wall forms a substantially corrugated surface and the inner wall forms a substantially smooth surface.

7. The graft of claim 5 wherein the fluid is a curable composition.

8. The graft of claim 7 wherein the curable composition is selected from the group consisting of a monomer, a liquid pre-polymer and an un-linked polymer.

9. The graft of claim 1 wherein the radially oriented non-distorting web support retains spacing and orientation of the inner wall relative to the outer graft wall with the addition of fluid.

10. The tubular shaped graft of claim 1 having a first and second end wherein an outer diameter of the first graft end is different than the outer diameter of the second graft end.

11. A method of treating cerebral aneurysm comprising the steps of:
   a. Selecting a graft having an inflated diameter compatible with an un-diseased body lumen and providing a graft design that, when deployed across the aneurysm, will effectively exclude the aneurysm from circulation and reinforce the weak blood vessel wall;
   b. inserting a flexible two walled graft of non-compliant material within the tortuous, narrow or stenotic cerebral blood vessels utilizing a catheter having a fluid conveying component and where the graft further comprises
   (i) two walls fluid sealed at each end of the graft and forming fluid chambers between the walls where said fluid chambers are bordered by at least one fused junction;

(ii) a plurality of non-distorting web supports oriented in a substantially radial direction within the fluid chambers and said web reinforcements are attached to the two walls;

(iii) at least one fused juncture wherein each fused juncture forms a circumference with a fixed diameter around the graft and wherein the fused juncture is not subject to inflation pressure and where the graft can bend without kinking or deforming;

(iv) a controllable valve accessing the fluid chambers between the walls of the graft and attachable to the fluid conveying component of the catheter;

c. maneuvering the graft to a selected location within the cerebral blood vessel lumen proximate to the aneurysm;

d. inserting fluid through a controllable valve within the graft into the fluid chambers between the two walls of the graft;

e. continuing the addition of fluid to deploy the graft in a radial direction sufficient that an outer wall of the graft contacts an un-diseased portion of the cerebral vessel lumen and a lumen is opened within the graft in communication with the cerebral vessel lumen;

f. continuing the addition of fluid to cause the graft wall to stiffen and isolate the aneurysm from the vessel lumen;

g. withdrawing the catheter; and h. continuing use of the stiffened graft to reinforce the vessel wall, isolate the aneurysm and maintain the graft lumen in communication with the vessel lumen.

12. The method of claim 11 further comprising inserting a graft containing at least one fenestration and orienting the fenestration to a branch of the vessel lumen.

13. A method of treating cerebral atheroscierosis comprising the steps of:

a. selecting a graft having a predetermined size and shape including side fenestrations;

b. inserting through the lumen of a tortuous, narrow or stenotic cerebral blood vessel a flexible two walled graft of non-compliant material utilizing a catheter having a fluid conveying component and where the graft further comprises (ii) a first outer wall and a second inner wall fluid sealed at each end of the graft;

(iii) one or more fused junctures of the inner wall and the outer wall wherein each fused juncture forms a circumference with a fixed diameter around the graft, wherein the graft can bend without kinking or distorting and the fused juncture is not subject to fluid pressure and the fused junctures create fluid tight seals and fluid communicating passages within resulting fluid chambers between the first and second walls;

(iv) a plurality of separate narrow and non-distorting web supports oriented in a substantially radial direction within the fluid chambers and attached to the first and second walls;

(iii) a controllable valve accessing the fluid chambers between the walls of the graft and attachable to the fluid conveying component of the catheter;

c. maneuvering the graft into an area of atherosclerosis within the vessel lumen;

d. inserting fluid through a controllable valve within the graft into the fluid chambers between the two walls of the graft;

e. continuing the addition of fluid to deploy the graft in a radial direction sufficient that the graft achieves a preselected shape without distortion and the outer wall of the graft contacts the vessel wall and the inner diameter of the vessel lumen is expanded and a smooth inner wall lumen is opened within the graft in communication with the vessel lumen;

f. continuing the addition of fluid to cause the graft wall to stiffen and the graft lumen expand to a selected diameter trapping residue or plaque between the graft and vessel wall;

g. withdrawing the catheter; and h. continuing use of the stiffened graft to reinforce the vessel wall, maintain the expanded vessel lumen and maintain the graft lumen in communication with the vessel lumen.

14. The method of claim 13 further comprising a tubular shaped graft containing a side fenestration at a selected location to allow deployment across bifurcating blood vessels.

15. A cerebral graft shaped for passage through and placement in the tortuous, narrow or stenotic cerebral circulatory system comprising:

a. a first hollow flexible non-compliant component having an open first proximal end and an open second distal end and forming an outer wall of a graft;

b. a second hollow flexible non-compliant component having a first open proximal end and a second open distal end and forming an inner wall of the graft;

c. a fluid tight seal joining the ends of the first and second components and a fluid impermeable seal joining the second ends of the first and second components forming a two walled lumen;

d. the first outer wall of the graft has an uneven surface and the second inner wall has a smooth surface;

e. at least one fused juncture of the outer and inner walls containing a fluid passageway wherein said juncture forms a non expanding circumference around the graft allowing the lumen to bend without kinking or distortion at the fused juncture;

f. a valve to convey fluid through the graft wall into fluid chambers between circumferentially oriented fused junctures and the sealed ends of the outer wall and inner wall of the lumen to inflate the graft to a pre-selected shape without distortion;

g. a plurality of flexible non-elastic web reinforcements within the fluid chambers and attached to the outer wall and inner wall wherein the length of the non-distorting web support tapers proximate to the fused juncture; and h. the addition of fluid into the fluid chambers to expand a vessel lumen.

16. The graft of claim 15 wherein the web supports are of varying length to cause the outer wall surface to be corrugated to prevent the drag force of the flowing blood through the graft from displacing the graft and to provide sites for neointimal growth.

* * * * *

UNITED STATES PATENT AND TRADEMARK OFFICE
CERTIFICATE OF CORRECTION

| | |
|---|---|
| PATENT NO. | : 7,468,072 B2 |
| APPLICATION NO. | : 10/540999 |
| DATED | : December 23, 2008 |
| INVENTOR(S) | : Hesham Morsi |

It is certified that error appears in the above-identified patent and that said Letters Patent is hereby corrected as shown below:

At Column 1, line 60, replace ~~shent~~ with stent.

At Column 4, line 26, add closing parentheses (about one millimeter 29).

At Column 4, line 29, replace ~~if~~ with in.

At Column 4, line 32, delete d in pressurize~~d~~.

At Column 4, line 42, add the following deployment of the invention across.

At Column 5, line 40, described.

At Column 6, line 22 claim 2, replace ~~iunctures~~ with junctures.

Signed and Sealed this

Seventeenth Day of February, 2009

JOHN DOLL
*Acting Director of the United States Patent and Trademark Office*